United States Patent [19]
Smith et al.

[11] Patent Number: 5,601,548
[45] Date of Patent: Feb. 11, 1997

[54] OPEN ANGLE GLAUCOMA TREATMENT APPARATUS AND METHOD

[75] Inventors: G. Richard Smith, Fountain Hills, Ariz.; John T. LiVecchi, Scranton, Pa.

[73] Assignee: Ophthalmic International, L.L.C., Fountain Hills, Ariz.

[21] Appl. No.: 334,935

[22] Filed: Nov. 7, 1994

[51] Int. Cl.⁶ ................................................... A61B 17/00
[52] U.S. Cl. ................................ 606/1; 606/207; 604/294
[58] Field of Search ........................ 606/1, 3, 6, 161, 606/201, 204.25, 202, 107, 166; 128/650, 651; 601/13; 625/5; 604/902

[56] References Cited

U.S. PATENT DOCUMENTS

| | | |
|---|---|---|
| 3,995,635 | 12/1976 | Higuchi et al. . |
| 4,282,882 | 8/1981 | Langham . |
| 4,558,698 | 12/1985 | O'Dell . |
| 4,619,259 | 10/1986 | Graybill et al. ...................... 606/166 |
| 4,739,761 | 4/1988 | Grandon ............................... 606/166 |
| 4,796,623 | 1/1989 | Krasner et al. ....................... 606/166 |
| 5,009,660 | 4/1991 | Clapham ............................... 606/166 |
| 5,108,427 | 4/1992 | Majercik et al. . |
| 5,171,254 | 12/1992 | Sher . |
| 5,196,027 | 3/1993 | Thompson et al. . |
| 5,308,355 | 5/1994 | Dybbs .................................. 606/166 |
| 5,382,243 | 1/1995 | Mulholland .......................... 604/301 |

*Primary Examiner*—Robert A. Hafer
*Assistant Examiner*—Justine Yu
*Attorney, Agent, or Firm*—Meschkow & Gresham, P.L.C.

[57] ABSTRACT

An open angle glaucoma treatment method and apparatus wherein pressure, positive or negative, is applied to the frontal surface of the eye. The open angle glaucoma treatment apparatus is a vacuum source and a vacuum applicator coupled by a hose. The vacuum applicator is an eye ring or an eye cup that is placed on the frontal surface of an eye. Suction (negative pressure) in the range of 10 to 30 mm. Hg. is applied by the vacuum source, which will fixate the ring or cup to the eye, or alternatively pressure is applied via ring or cup that is held in place. The suction or pressure is applied for 15 to 120 seconds. A second treatment is recommended later. It could be within twelve hours, on the following day, or within the next couple of days. A second treatment more than five days later considered less effective or ineffective.

12 Claims, 2 Drawing Sheets

OPEN ANGLE GLAUCOMA TREATMENT APPARATUS AND METHOD

BACKGROUND OF THE INVENTION

1. Field of the Invention

This invention relates to the treatment of open angle glaucoma.

More particularly, the present invention relates to an open angle glaucoma treatment comprising the application of negative pressure to the surface of the eye.

In a further and more specific aspects, the invention relates to open angle glaucoma treatment apparatus and method including an automated application of negative pressure to the frontal surface of the eye for a proscribed period of time.

2. Prior Art

It is widely known that open angle glaucoma is a serious illness affecting the eyes. The condition of open angle glaucoma is characterized by an increase in the pressure within a person's eye or eyes, called the inter-ocular pressure, or as used herein IOP.

The IOP of a normal eye should be less than 20 millimeters of mercury (hereafter mm. Hg.) An IOP slightly above 20 mm. Hg. is suspect; an IOP of about 25 mm. Hg. or more is considered to be a symptom of open angle glaucoma.

If left untreated, open angle glaucoma can lead to serious loss of eyesight or blindness. Nearly all standard eye examinations, including one usually given to children in grade school, include a checking for elevated IOP.

The art is replete with various apparatus and methods of treatment used to treat or reverse the causes and symptoms of open angle glaucoma. These typically include surgical procedures; lasers; drugs; and eye drops. Surgery involves cutting the eye; lasers cut through tissue in the interior of the eye; drugs are ingested, or in the case of one prescriptive medication generally illegal to possess in most of the United States, smoken (marijuana); and eye drops are placed in the eye to retard production of the aqueous fluid in the eye.

Side effects from the drugs and drops range from loss of vision to elevated blood pressure to heart attacks and strokes. Surgery, whether by scalpel or laser, runs the risk attendant with local or general anaesthetics, incorrect performance by the surgeon (with serious side effects), and can have a long and painful recovery period even when all goes as planned.

It would be highly advantageous, therefore, to remedy the foregoing and other deficiencies inherent in the prior art.

Accordingly, it is an object of the present invention to provide improvements in open angle glaucoma treatment apparatus and an open angle glaucoma treatment method that is non-invasive.

Another object of the invention is the provision of improvements in open angle glaucoma treatment apparatus and an open angle glaucoma treatment method that carry no side effects.

And another object of the invention is to provide improved means for treating open angle glaucoma that is applied to the frontal surface of the eye.

Still another object of the immediate invention is the provision of an improved vacuum applicator to be placed on the frontal surface of the eye, and a vacuum source, for generating suction against the eye.

Yet another object of the invention is to provide means for reducing the pressure within an eye by placing an eye ring or cup on the eye, and generating vacuum to that eye ring or cup within 10 to 30 mm. Hg.

Yet still another object of the invention is the provision of improved means for timing how long pressure is applied to the eye.

A further object of the instant invention is to provide improvements in open angle glaucoma treatment where a treatment takes 15 to 120 seconds.

And a further object of the invention is the provision of an open angle glaucoma treatment which is administered on once day, and a follow-up treatment which is administered no less than twelve hours or more than five days later.

Yet a further object of this invention is to provide an automatic vacuum unit integrated with an adjustable timer.

And yet an object of the invention is the provision of means and improvements according to the foregoing which will materially reduce the cost, and materially increase the efficiency of treating open angle glaucoma.

An additional object of the invention is to provide for a newly designed eye ring that provides suction around the eye and directly on the Canal of Schlemm area without applying pressure to the cornea.

SUMMARY OF THE INVENTION

Briefly, to achieve the desired objects of the instant invention in accordance with a preferred embodiment thereof, first provided is open angle glaucoma treatment apparatus comprising a vacuum source and a vacuum applicator. The vacuum source and a vacuum applicator are coupled by a hose.

The vacuum applicator is an eye ring or an eye cup that is placed on the frontal surface of an eye. Suction (negative pressure) in the range of 10 to 30 mm. Hg. is applied by the vacuum source, which will fixate the ring or cup to the eye. The suction is applied for 15 to 120 seconds. In a highly effective embodiment of the invention an eye ring designed to provide suction only to the Canal of Schlemm area without applying pressure to the cornea is used.

A second application of suction (approximately the same pressure and the for the same time) is recommended later. It could be within twelve hours, on the following day, or within the next couple of days. A second treatment should generally be completed within no more than five days later than the first treatment. Alternatively, pressure can be applied.

BRIEF DESCRIPTION OF THE DRAWINGS

The foregoing, further, and more specific objects and advantages of the instant invention will become readily apparent to those skilled in the art from the following detailed description of a preferred embodiment thereof taken in conjunction with the drawings, in which.

PREFERRED EMBODIMENT OF THE PRESENT INVENTION

Figure 1:
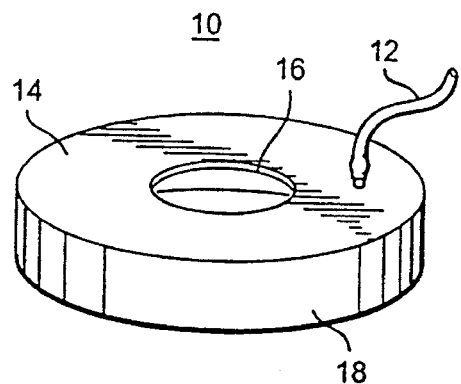
FIG. 1 is a perspective view of an eye ring with hose attached.

Turning now to the drawings in which like reference characters indicate corresponding elements throughout the several views. Attention is first directed to FIG. 1.

Figure 5:
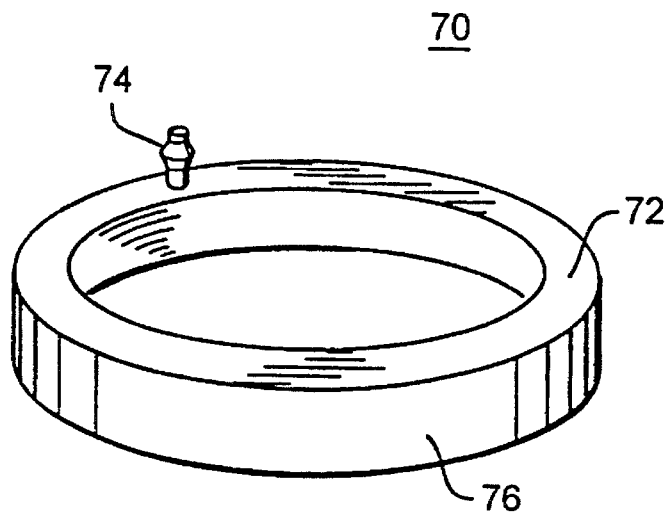
FIG. 5 is a perspective view of a new design for an eye ring having an outer annular wall with a wide outer perimeter and a narrow gap between the inner and outer annular walls.

Shown in FIG. 1 is eye ring 10. Eye ring 10 has top 14, annular hole 16, and annular wall 18. Also shown is a segment of hose 12. As will be appreciated from the description below, hose 12 is a continuous hose coupling eye ring 10 and the control unit. Hose 12 couples to eye ring 10 via a hose coupler (hidden from view). An exemplary hose coupler 74 is illustrated in FIG. 5.

Figure 2:
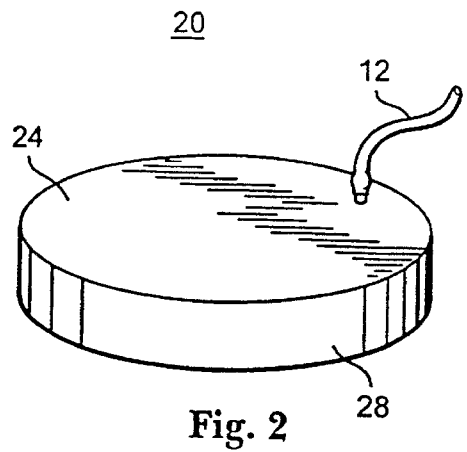
FIG. 2 is a perspective view of an eye cup with hose attached.

Shown in FIG. 2 is eye cup 20. Eye cup 20 has top 24 and annular wall 28. A similar segment of hose 12 is also shown. As will be appreciated from the description below, hose 12 is a continuous hose coupling eye cup 20 and the control unit. As with eye ring 10, hose 12 couples to eye cup 20 via a hose coupler (hidden from view).

In performing conventional manual lamellar keratoplasty over astigmatic keratotomy, a pneumatic fixation ring much like eye ring 10 is placed with the center hole over the cornea and the outer ring over the iris of an eye. In the foregoing procedure, the cornea is removed by guiding a scalpel or other cutting device over the top of the fixation ring. No such cutting is need for the present invention, although similarly for the present invention a pneumatic fixation ring much like eye ring 10 is placed with the center hole over the cornea and the outer ring over the iris of an eye. An eye cup, which is similar to the ring, but with no center hole, can alternatively be used for the present invention.

With respect to the present invention, eye ring 10 is placed with hole 16 over the cornea and annular wall 18 around or about the iris of an eye which has been diagnosed as having a sufficiently high IOP to be considered open angle glaucoma. Alternately, eye cup 20 is placed over the eye which has been diagnosed as having a sufficiently high IOP to be considered open angle glaucoma. Annular wall 28 is centered around or about the iris or limbus of an eye.

Figure 3:
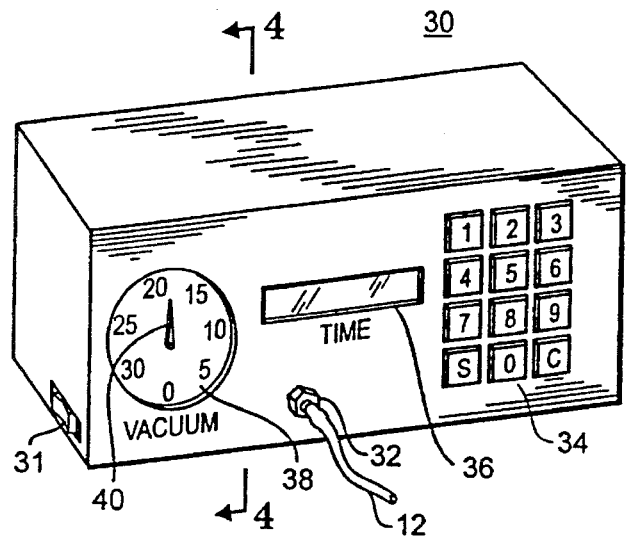
FIG. 3 is a perspective view of a vacuum control unit showing time and vacuum displays, and a keypad for setting the amount of time vacuum is to be applied.

Extending from eye ring 10 and eye cup 20 is a first end of hose 12. As shown in FIG. 3, the second end of hose 12 connects to control unit 30 at hose connector 32. Within the center of hose connector 32 is a hole in which the second end of hose 12 is inserted.

Control unit 30 also has keypad 34, time display 36, and vacuum display 38. An on/off switch 31 may be included for convenient operation.

Not shown within control unit 30 is the circuitry for the controls, and the vacuum pump. These are well known to those skilled in the art.

Keypad 34 has numeric keys labeled 1 through 9 and keys labeled "S" or "Start" and "C" or "Cancel". The numeric keys are used to enter the amount of time the vacuum pump is to run, and that time is displayed on display 36.

Vacuum display 38 is labeled -5 through -30 and indicates vacuum in mm. Hg. Vacuum indicator 40 is a line or dot displaying the vacuum pressure being applied by the vacuum pump in a real-time manner.

Figure 4:
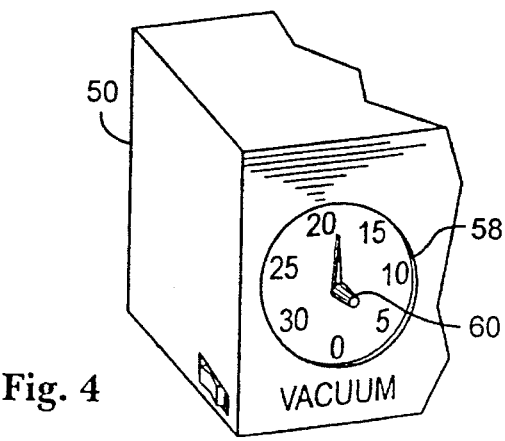
FIG. 4 is a perspective view of the portion of a an alternate vacuum control unit from the section of FIG. 3 shown to the left of line 4—4, where the vacuum displays also comprises a control knob for setting the amount of vacuum to be applied.

An alternate embodiment of control unit 30 is shown in FIG. 4 and labeled control unit 50. The two control units are analogous to one another, except that vacuum dial 58 has an internal vacuum adjustment switch (not shown) which connects to vacuum adjustment switch knob 60. Using control unit 50, the user can adjust the amount of vacuum applied.

After placing eye ring 10 or eye cup 20 on the patient, the treatment provider either turns on control unit 30 or 50, or plugs in a control unit. Using keypad 34, the provider sets the amount of time for the treatment, generally within the range of 15 to 120 seconds, and certainly for no more than three minutes, or damage to the eye may occur. The setting is displayed by display 36. If an incorrect setting is entered, the provider may depress the key marked "C" or "Cancel" and display 36 clears.

When the provider is satisfied with the time setting, pressing the "S" or "Start" key starts the vacuum pump. When the suction reaches a minimal level eye ring 10 or eye cup 20 adheres to the patient's eye. Any suction beyond the minimal level is applied to eye for the time indicated by display 38.

The vacuum pump in control unit 30 is self-regulating, and the suction reaches a pressure of 19 to 23 mm. Hg. Pressure with the 10 to 30 mm. Hg. has been found to be effective, but within the range of 19 to 23 mm. Hg. has been found to be most effective, generally causing a decrease in IOP of about 8 mm. Hg.

The vacuum pump in is not self-regulating, but rather will increase the suction from 0 to the amount set with knob 60 on vacuum dial 58. Control unit 50 offers the provider the greater flexibility, which will be required for patients with a more serious case of open angle glaucoma. Control unit 30 offers the provider a unit which simply needs to turned on and set for time, which is acceptable for most open angle glaucoma patients.

Figure 6:
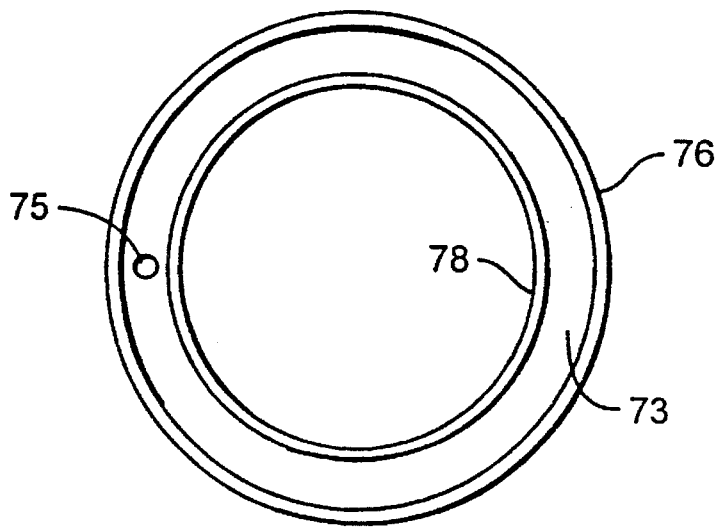
FIG. 6 is a bottom view of the new design for an eye ring shown in FIG. 5.

FIG. 5 shows eye ring 70. Eye ring 70 has outer annular wall 76, ring top 72, inner annular wall 78, and hose coupler 74. Outer annular wall 76 is spaced approximately 2 mm. from inner annular wall 78, defining a narrow suction gap. Eye ring 70 is designed to provide suction only to the Canal of Schlemm area without applying pressure to the cornea, providing for increased efficiency of the method and apparatus herein. FIG. 6 shows eye ring 70 from the bottom, and ring bottom 73 is the opposite side of ring top 72. Aperature 75 runs through hose coupler 74. Hose couplers such as hose coupler 12 are well known in the art. As described above, a similar hose coupler may be incorporated into eye ring 10 and eye cup 20.

It has been found with patient having a high IOP (approximately 35 or greater) that a second treatment at least twelve hours later, and generally on the following day, or within five days, will cause a subsequent decrease in pressure of about 8 mm. Hg. This effectively means that after two treatments, the patient has an IOP of 19 mm. Hg., considered to be normal.

It has also been found that the application of pressure has similar benefits to the application of vacuum. Those skilled in the art will recognize that pressure and vacuum are analogous, and constitute directly opposing forces.

In clinical studies the following results have been achieved:

Patient 1 is 69 years of age, and male.

Patient 2 is 51 years of age, and female.

Patient 3 is 38 years of age, and male.

Patient 4 is 36 years of age, and male.

| PATIENT | MM. HG. START (IN EACH EYE) | MM. HG. AFTER ONE TREATMENT (IN EACH EYE) | MM. HG. AFTER TWO TREATMENTS (IN EACH EYE) |
| --- | --- | --- | --- |
| Patient 1 | 29 and 31 | 23 and 24 | 20 and 21 |
| Patient 2 | 26 and 23 | 21 and 20 | 22 and 22 |
| Patient 3 | 21 and 23 | 20 and 20 | 16 and 17 |
| Patient 4 | 24 and 23 | 20 and 19 | 20 and 20 |

With Patient 1, the second treatment was five months after the first treatment. Subsequent treatments at five months post first, six months post first, nine months post first, and fifteen months post first yielded eye pressures of 18 and 18 mm. Hg.

With Patient 2, the second treatment was three days after the first treatment. Subsequent treatments at five days post first, seven days post first, 24 days post first, two months post first, and four months post first yielded eye pressures of 18 and 18 mm. Hg.

With Patient 3, the second treatment was two months after the first treatment. Subsequent treatments at nine months post first yielded eye pressures of 17 and 17 mm. Hg.

With Patient 4, the second treatment was nine months after the first treatment. Subsequent treatments at eighteen months post first, 25 months post first, 27 months post and 30 months post first yielded eye pressures of 16 and 16 mm. Hg.

While the effect of the treatment is not known with any surety, a plausible explanation has been hypothesized explaining why the open angle glaucoma treatment disclosed herein is effective. It is believed that the open angle glaucoma condition may be brought on when the trabecular meshwork in the eye collapses or clogs, thereby reducing the outflow of aqueous fluid. The instant method and apparatus is believed to unclog or reverse the collapse of the trabecular meshwork thereby allowing the aqueous fluid to flow normally.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An open angle glaucoma treatment apparatus comprising:

a vacuum source configured to produce an amount of vacuum; and a vacuum applicator coupled to said vacuum source, said vacuum applicator being configured to contact the frontal surface of an eye such that said amount of vacuum is introduced between said frontal surface of said eye and said vacuum applicator for a duration of time between 15 and 120 seconds; wherein said vacuum applicator has an outer annular wall sized to circumscribe an area of said frontal surface of said eye, said area being located over the Canal of Schlemm of said eye.

2. The open angle glaucoma treatment apparatus of claim 1, wherein said amount of vacuum is in the range of 10 to 30 millimeters Hg.

3. The open angle glaucoma treatment apparatus of claim 1, wherein said amount of vacuum is in the range of 19 to 23 millimeters Hg.

4. The open angle glaucoma treatment apparatus of claim 1, wherein said vacuum source and said vacuum applicator are coupled by a hose.

5. The open angle glaucoma treatment apparatus of claim 1, wherein said vacuum applicator is an eye ring.

6. The open angle glaucoma treatment apparatus of claim 5, wherein said eye ring is configured to contact the frontal surface of an eye such that said amount of vacuum is applied to an area located over said frontal surface of said eye without applying pressure to the center of the cornea of said eye.

7. The open angle glaucoma treatment apparatus of claim 5, wherein said eye ring has an outer annular wall, a ring top surface, and an inner annular wall spaced in the range of 1–3 millimeters from said outer annular wall.

8. The open angle glaucoma treatment apparatus of claim 1, wherein said vacuum applicator is an eye cup.

9. The open angle glaucoma treatment apparatus of claim 1, further comprising a timer coupled to said vacuum source.

10. The open angle glaucoma treatment apparatus of claim 9, wherein said vacuum source and said timer are integrated into a control unit.

11. The open angle glaucoma treatment apparatus of claim 10, wherein said control unit further comprises a keypad for controlling a duration of time that said amount of vacuum is applied to said eye.

12. The open angle glaucoma treatment apparatus of claim 10, wherein said control unit further comprises a keypad for controlling said amount of vacuum.

\* \* \* \* \*